United States Patent
Okumura et al.

(10) Patent No.: US 10,894,779 B2
(45) Date of Patent: Jan. 19, 2021

(54) PROCESS FOR PRODUCING FLUTAMETAMOL

(71) Applicant: GE HEALTHCARE LIMITED, Buckinghamshire (GB)

(72) Inventors: Yuki Okumura, Tokyo (JP); Gota Tonoya, Tokyo (JP); Tomoyuki Matsunami, Tokyo (JP); Kei Akama, Tokyo (JP)

(73) Assignee: GE HEALTHCARE LIMITED, Buckinghamshire (GB)

( * ) Notice: Subject to any disclaimer, the term of this patent is extended or adjusted under 35 U.S.C. 154(b) by 0 days.

(21) Appl. No.: 16/489,260

(22) PCT Filed: Feb. 22, 2018

(86) PCT No.: PCT/EP2018/054407
§ 371 (c)(1),
(2) Date: Aug. 27, 2019

(87) PCT Pub. No.: WO2018/158137
PCT Pub. Date: Sep. 7, 2018

(65) Prior Publication Data
US 2020/0062724 A1 Feb. 27, 2020

(30) Foreign Application Priority Data
Feb. 28, 2017 (JP) ................. 2017-037793

(51) Int. Cl.
*C07D 277/66* (2006.01)
*C07B 59/00* (2006.01)

(52) U.S. Cl.
CPC .......... *C07D 277/66* (2013.01); *C07B 59/002* (2013.01); *C07B 2200/05* (2013.01)

(58) Field of Classification Search
CPC .................................................... C07D 277/66
See application file for complete search history.

(56) References Cited

FOREIGN PATENT DOCUMENTS

| WO | 2007020400 A1 | 2/2007 |
|----|---------------|--------|
| WO | 2011044406 A1 | 4/2011 |
| WO | 2018158137 A1 | 9/2018 |

OTHER PUBLICATIONS

International Search Report and Written Opinion corresponding to International Application No. PCT/EP2018/054407, dated May 5, 2018.

*Primary Examiner* — Shawquia Jackson
(74) *Attorney, Agent, or Firm* — Jeff B. Vockrodt; Culhane Meadows, PLLC

(57) ABSTRACT

The present invention provides a process to enhance the productivity such as yield of radioactive fluorine labeled flutemetamol.

Provided is a process for producing a radioactive fluorine labeled flutemetamol, which comprises:

(a) a step of allowing a labeling precursor represented by the predetermined general formula to react with a radioactive fluoride ion in a presence of a solvent to obtain a radioactive fluorine labeled intermediate represented by the predetermined general formula, and (b) a step of removing the protecting groups from the radioactive fluorine labeled intermediate to obtain a radioactive fluorine labeled flutemetamol, in which the above step (a) is carried out at an internal temperature of reaction solution of 140° C. or higher.

15 Claims, 1 Drawing Sheet

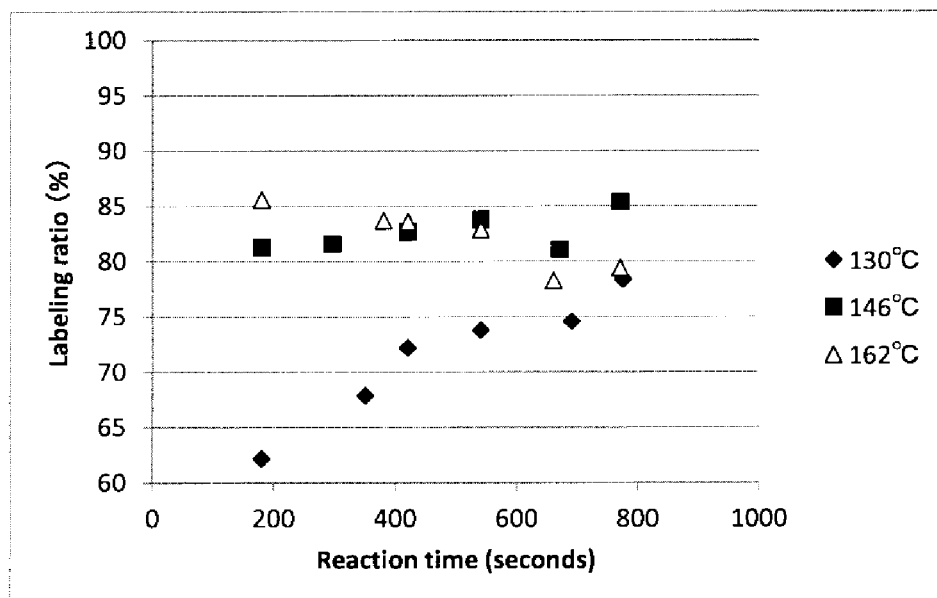

PROCESS FOR PRODUCING FLUTAMETAMOL

CROSS-REFERENCE TO RELATED APPLICATIONS

This application is a filing under 35 U.S.C. 371 of international application number PCT/EP2018/054407, filed Feb. 22, 2018, which claims priority to application number 2017-037793 filed in Japan on Feb. 28, 2017, the entire disclosures of each of which are hereby incorporated by reference.

TECHNICAL FIELD OF THE INVENTION

The present invention relates to a process for producing flutemetamol.

BACKGROUND OF THE INVENTION

Flutemetamol [$^{18}$F] Injection is a reagent used for visualizing beta-amyloid plaques in the brain with a positron emission tomography, and is useful for diagnosis of Alzheimer dementia.

As a process for producing [$^{18}$F]flutemetamol, known is a process in which a precursor AH111907 (6-ethoxymethoxy-2-(4'-(N-formyl-N-methyl)amino-3'-nitro)phenylbenzothiazole) is allowed to react with a radioactive fluoride using a radiopharmaceutical synthesis platform "FASTlab™" so as to effect a radiofluorination reaction that substitutes the nitro group of AH111907 with $^{18}$F, thereafter a strong base is used to convert the residual AH111907 to less lipophilic compounds, and the protecting groups for the hydroxyl and amino groups of the $^{18}$F-substituted product of AH111907 (6-ethoxymethoxy-2-(4'-(N-formyl-N-methyl)amino-3'-[$^{18}$F]fluoro)phenylbenzothiazole) are removed, followed by purification using a solid phase extraction (SPE) cartridge (WO2011/044406).

On the other hand, WO2007/020400 discloses that radiofluorination reaction for anilide derivatives can be performed at a non-extreme temperature (for example, 15-180° C.), preferably at an elevated temperature of 80-150° C. (for example, around 120° C.), and is suitably performed in an anhydrous organic solvent or may be performed in some case in an organic solvent containing a low level of water.

However, the processes disclosed in Patent Literatures 1 and 2 are low in yield of [$^{18}$F]flutemetamol, and thus cannot afford mass production providing for a wide area of delivery. Thus, a further improvement of productivity such as yield is demanded for supplying more [$^{18}$F]flutemetamol preparations.

SUMMARY OF THE INVENTION

The present invention has been made in light of the above described circumstances, and aims at enhancing the productivity such as yield of [$^{18}$F]flutemetamol without quality degradation.

According to one aspect of the present invention, there is provided a process for producing a radioactive fluorine labeled flutemetamol, which comprises:
(a) a step of allowing a labeling precursor represented by the following general formula (1) to react with a radioactive fluoride ion in a presence of a solvent to obtain a radioactive fluorine labeled intermediate represented by the following general formula (2), and
(b) a step of removing the protecting groups from the radioactive fluorine labeled intermediate to obtain a radioactive fluorine labeled flutemetamol,
in which the above step (a) is carried out at an internal temperature of reaction solution of 140° C. or higher,

[Chemical Formula 1]

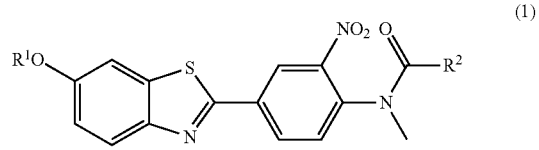

(1)

where, in the above general formula (1), $R^1$ is a protecting group for the hydroxyl group, and $C(O)R^2$ is a protecting group for the amino group,

[Chemical Formula 2]

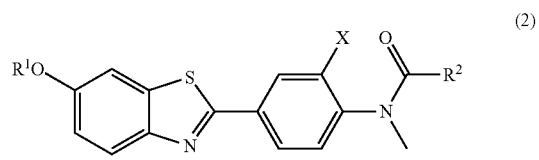

(2)

where, in the above general formula (2), $R^1$ and $R^2$ are as defined in the above general formula (1), and X is a radioactive fluorine.

Effect of the Invention

The present invention performs the radiofluorination reaction in a solvent whilst the inner temperature of the reaction solution is maintained at 140° C. or higher, and thus can enhance the yield of radioactive fluorine labeled flutemetamol and shorten the production time without quality being degraded, thereby improving productivity.

BRIEF DESCRIPTION OF DRAWING

FIG. 1: A graph showing the results of study of temperature conditions of radiofluorination reaction made in Example of the present application, in which ♦ represents the results at a set temperature of 150° C. (an inner temperature of 130° C.), ■ represents the result at a set temperature of 170° C. (an inner temperature of 146° C.), and Δ represents the result at a set temperature of 190° C. (an inner temperature of 162° C.).

DEFINITIONS

The term "alkyl" used alone or as part of another group in the present specification refers to a straight-chain or branched-chain saturated hydrocarbon group represented by a formula $—C_nH_{2n+1}$ (wherein n≥1), such as methyl, ethyl, propyl, isopropyl, butyl, isobutyl, tert-butyl, n-pentyl or n-hexyl.

Further, the term "haloalkyl" used alone or as part of another group in the present specification refers to an alkyl in which one or more hydrogen has been substituted with a halogen such as fluorine, chlorine, bromine or iodine.

Further, the term "alkoxy" used alone or as part of another group in the present specification refers to a straight-chain or branched-chain group represented by a formula —OC$_n$H$_{2n+1}$ (wherein n≥1), such as methoxy, ethoxy, propoxy, isopropoxy, butoxy, isobutoxy, tert-butoxy, n-pentoxy or n-hexyloxy.

Further, the term "aryl" used alone or as part of another group in the present specification refers to a monocyclic or condensed-cyclic aromatic hydrocarbon such as phenyl or naphthyl.

Further, the term "radioactive fluorine" in the present specification encompasses various radioisotopes of fluorine, and preferably refers to [$^{18}$F]fluorine.

(a) Radiofluorination Step

In the radiofluorination step (a) in the present invention, a radiofluorination reaction is carried out by allowing a labeling precursor represented by the above general formula (1) to react with a radioactive fluoride ion in a presence of a solvent to obtain a radioactive fluorine labeled intermediate represented by the above general formula (2).

As R$^1$ representing a protecting group for the hydroxyl group, can be used one which is described in Greene's Protective Groups in Organic Synthesis (the fifth edition, published by John Wiley & Sons Inc. on Oct. 27, 2014) preferably such that the group represented by —OR$^1$ is an alkoxymethoxy group having 1-6 carbon atoms, concrete examples of which include an ethoxymethoxy group and a methoxymethoxy group. The contents of the Greene's Protective Groups in Organic Synthesis are incorporated herein by reference.

R$^2$ is selected from hydrogen, an alkyl having 1-10 carbon atoms, a haloalkyl having 1-10 carbon atoms, an aryl having 6-14 carbon atoms, an arylalkyl having 6-14 carbon atoms and a group represented by —(CH$_2$CH$_2$O)$_p$—CH$_3$ (wherein p is an integer of 1-10). R$^2$ is preferably hydrogen or an alkyl having 1-10 carbon atoms, more preferably hydrogen or methyl, and still more preferably hydrogen.

The above labeling precursor can be synthesized by, for example, a method described in WO2007/020400. A preferred example of the above labeling precursor is 6-ethoxymethoxy-2-(4'-(N-formyl-N-methyl)amino-3'-nitro)phenylbenzothiazole (AH111907), and an example of the synthesis method thereof is described in Example 1 of WO2007/020400. The contents of WO2007/020400 are incorporated herein by reference.

Radioactive fluoride ions can be obtained by, for example, adding a cationic counterion to an aqueous solution containing [$^{18}$F]fluoride ions obtained from [$^{18}$O]water via $^{18}$O(p,n)$^{18}$F nuclear reaction, and then removing water therefrom. The cationic counterion is preferably one that has a sufficient solubility in an anhydrous reaction solvent so that the solubility of [$^{18}$F]fluoride ions is maintained. Examples thereof include alkali metal ions (sodium ion, potassium ion, cesium ion and rubidium ion) that form a complex with a phase transfer catalyst (for example, 4,7,13,16,21,24-hexaoxa-1,10-diazabicyclo[8.8.8]hexacosane (tradename; CRYPTOFIX 2.2.2)), and tetraalkylammonium, and preferred is tetrabutylammonium. [$^{18}$F]tetrabutylammonium fluoride can be prepared by, for example, passing the [$^{18}$F]fluoride ion-containing [$^{18}$O]water obtained via the $^{18}$O(p,n)$^{18}$F nuclear reaction through an anion exchange resin so as to have the [$^{18}$F]fluoride ion adsorbed by the anion exchange resin, and eluting the same using a tetrabutylammonium hydrogencarbonate aqueous solution, followed by azeotropic distillation in acetonitrile.

The solvent used in the above radiofluorination step (a) is not specifically limited as far as the radiofluorination reaction can be carried out, but preferably comprises at least one of an organic solvent and water, more preferably is an organic solvent containing 2000 ppm or lower of water and particularly preferably an organic solvent containing 10-1000 ppm of water. The organic solvent is preferably a water-soluble organic solvent or a polar organic solvent, and concrete examples thereof include acetonitrile, dimethylformamide, dimethylsulfoxide, dimethylacetamide, tetrahydrofuran, dioxane, 1,2-dimethoxyethane, sulfolane, N-methylpyrrolidone, or ionic liquids including imidazolium derivatives such as 1-ethyl-3-methylimidazolium hexafluorophosphate, pyridinium derivatives such as 1-butyl-4-methylpyridinium tetrafluoroborate, phosphonium compounds or tetraalkylammonium compounds. Among these, dimethylsulfoxide is preferred.

The reaction temperature in the above radiofluorination step (a) is 140° C. or higher, preferably 145-170° C., more preferably 150-165° C. which is the internal temperature of the reaction solution subjected to the radiofluorination reaction. By setting the reaction temperature at 140° C. or higher, high yield can be achieved for a short time. The reaction time in the above radiofluorination step (a) is preferably 3-10 minutes, more preferably 4-6 minutes. As a reaction vessel, a glass vessel or a plastic vessel resistant to the solvent can be used. A heater which can be used is not specifically limited but includes, for example, a block heater or an air heater.

(b) Deprotection Step

In the deprotection step (b) in the present invention, the protecting groups are removed from the radioactive fluorine labeled intermediate obtained in the above step (a) to obtain a radioactive fluorine labeled flutemetamol. Specifically, the hydroxyl protecting group represented by R$^1$ and the amino protecting group represented by R$^2$ are each removed from the radioactive fluorine labeled intermediate represented by the general formula (2) to obtain a radioactive fluorine labeled flutemetamol. The radioactive fluorine labeled intermediate which is subjected to the deprotection step (b) may be an unpurified radioactive fluorine labeled intermediate as it is obtained in the above step (a), or a radioactive fluorine labeled intermediate that has been purified by subjecting a reaction mixture obtained in the above step (a) to a purification step. As the purification step, can be used not only a step employing an ordinary purification method but also other steps such as the below-mentioned precursor decomposition step (a1) and the below-mentioned first purification step (a2).

The above deprotection step (b) may be carried out as described in Greene's Protective Groups in Organic Synthesis (the fifth edition, published by John Wiley & Sons Inc. on Oct. 27, 2014), and it is preferred that an acid hydrolysis using an organic acid or inorganic acid is performed when an acetal as a protecting group is deprotected, As the acid, an inorganic acid such as sulfuric acid, hydrochloric acid, phosphoric acid and hydrobromic acid is preferably used, and hydrochloric acid is used more preferably.

The deprotection step (b) in the present invention can be carried out in a presence of water, an organic solvent such as alkyl alcohols having 1-4 carbon atoms or acetonitrile, or a mixed liquid of these, and is advantageously carried out by adding the acid to an eluted ethanol solution resulting from the elution step of the below-mentioned first purification step (a2) which has been conducted after the below-mentioned precursor decomposition step (a1) following the above step (a).

The deprotection step (b) in the present invention is carried out at preferably 100° C. or higher, more preferably 120-140° C. which is an internal temperature of the reaction solution subjected to the deprotection reaction.

Steps (a1) and (a2) Prior to Deprotection Step (b)

As mentioned above, a radioactive fluorine labeled intermediate that has been purified from a reaction mixture obtained in the above step (a) may be subjected to the deprecation step (b) in the present invention. As a purification process, the below-mentioned precursor decomposition step (a1) and the below-mentioned first purification step (a2) are preferably used. By performing the below-mentioned precursor decomposition step (a1) and the below-mentioned first purification step (a2) prior to the deprotection step (b), highly-polar compounds resulting from the labeling precursor can be removed prior to the deprotection step (b). As a result, the radioactive fluorine labeled intermediate can be purified while the loss of the radioactive fluorine labeled intermediate which is an intermediate compound for the radioactive fluorine labeled flutemetamol is prevented. Therefore, the radioactive fluorine labeled flutemetamol can be obtained with a higher yield than before and with a quality comparable to conventional one, thereby making it possible to enhance the productivity of the radioactive fluorine labeled flutemetamol.

Precursor Decomposition Step (a1)

In the precursor decomposition step (a1), a strong base is allowed to act on a reaction mixture resulting from the above step (a), which contains the labeling precursor and the radioactive fluorine labeled intermediate. As a result, the labeling precursor which is a residue contained in the reaction mixture resulting from the above step (a) is converted to highly-polar compounds. These highly-polar compounds include those shown in FIG. 1 of WO 2011/044406. Meanwhile, the radioactive fluorine labeled intermediate does not react with the strong base but remains unchanged in the precursor decomposition step (a1).

The strong base includes alkali metal alkoxides, alkali metal hydroxides and the like, and is preferably sodium methoxide, sodium ethoxide, sodium hydroxide, potassium hydroxide, sodium hydride or sodium methylmercaptan, more preferably sodium methoxide or sodium ethoxide, and still more preferably sodium methoxide.

The precursor decomposition step (a1) is preferably carried out in a presence of a solvent. The solvent includes alkyl alcohols, and is preferably methanol.

The precursor decomposition step (a1) can be carried out within a temperature range of, for example, 15-180° C., preferably 80-150° C., more preferably 100-140° C., and still more preferably 120-130° C. which is an internal temperature of the reaction solution subjected to the precursor decomposition reaction.

The First Purification Step (a2)

In the first purification step (a2), the radioactive fluorine labeled intermediate is purified using a reverse phase solid phase extraction (SPE) cartridge after the precursor decomposition step (a1). As a result, the radioactive fluorine labeled intermediate is separated from the highly-polar compounds resulting from the precursor decomposition step (a1).

As the reverse phase SPE cartridge, can be used one packed with fillers having a silyl group modified with an alkyl containing preferably not less than 8 carbon atoms, more preferably not less than 18 carbon atoms, and still more preferably used is a reverse phase SPE cartridge packed with triacontyl-silylated silica gel in which silyl groups are modified with an alkyl containing 30 carbon atoms. Such a reverse phase SPE cartridge is commercially available from, for example, Macherey-Nagel. The reverse phase SPE cartridge is preferably conditioned with acetonitrile and water prior to use.

Purification of the radioactive fluorine labeled intermediate using the reverse phase SPE cartridge is not specifically limited as far as it is carried out using an ordinary technique of the solid phase extraction method. An example thereof is explained below.

First, a radioactive fluorine labeled intermediate that has undergone the precursor decomposition step (a1) is retained in a reverse phase SPE cartridge (retaining step (a2-1)). Preferably, after the precursor decomposition step (a1), the resulting reaction solution containing the radioactive fluorine labeled intermediate and the above-described highly-polar compounds is diluted by adding water thereto, and then the resultant is loaded into the reverse phase SPE cartridge.

Next, the reverse phase SPE cartridge is washed with a mixed liquid of water with at least one organic solvent selected from the group consisting of acetonitrile, tetrahydrofuran and alkyl alcohols containing 1-3 carbon atoms (washing step (a2-2)). The solvent used for washing is preferably a mixed liquid of water with acetonitrile As a mixing proportion thereof, mention may be made of, for example, the content of acetonitrile being 35-45 vol. %, preferably 39.5-40.5 vol. % relative to the entire mixed liquid. The temperature of the reverse phase SPE cartridge is preferably in the range of 19-34° C., more preferably in the range of 20-30° C. The washing step may be repeated several times. As a result, the above described highly-polar compounds can be eluted from the reverse phase SPE cartridge whilst the radioactive fluorine labeled intermediate is retained in the reverse phase SPE cartridge.

Thereafter, the radioactive fluorine labeled intermediate is eluted from the reverse phase SPE cartridge by use of an alkyl alcohol containing 1-3 carbon atoms (eluting step (a2-3)). The alkyl alcohol containing 1-3 carbon atoms includes methanol, ethanol, 1-propanol and 2-propanol, and is preferably ethanol from the viewpoint of safety. In this instance, nitrogen gas may be allowed to flow into the reverse phase SPE cartridge from an injection port thereof, or suction may be applied to an outlet thereof. The obtained eluate can be used in the next deprotection step (b) as it is, or after it is concentrated by removing the solvent by heating or under reduced pressure.

Steps (b1) and (b2) Posterior to Deprotection Step (b)

The radioactive fluorine labeled flutemetamol obtained in the deprotection step (b) in the present invention can be subjected to a further purification step before it is processed into a preparation. The further purification step can be carried out by, for example, the below-mentioned second purification step (b1) and the below-mentioned third purification step (b2).

The Second Purification Steps (b1)

The second purification step (b1) can be carried out using, for example, a reverse phase SPE cartridge.

As a reverse phase SPE cartridge used in the second purification step (b1), can be used any type of those that can be used in the first purification step (a2), and is preferably used a reverse phase SPE cartridge packed with triacontyl-silylated silica gel in which silyl groups are modified with an alkyl having 30 carbon atoms.

Purification of the radioactive fluorine labeled flutemetamol using the reverse phase SPE cartridge is not specifically limited as far as it is carried out using an ordinary technique of the solid phase extraction method. An example thereof is explained below.

First, a radioactive fluorine labeled flutemetamol that has undergone the deprotection step (b) is retained in a reverse phase SPE cartridge (retaining step (b1-1)). Preferably, after the deprotection step (b), a crude product of the radioactive fluorine labeled flutemetamol is diluted by adding thereto water so as to adjust the content of an organic solvent originating from a previous step (for example, ethanol or the like brought from the first purification step (a2)) to 50 vol. % or lower, and then the resultant is loaded into the reverse phase SPE cartridge.

Next, the reverse phase SPE cartridge is washed with water or a mixed liquid of water with at least one organic solvent selected from the group consisting of acetonitrile, tetrahydrofuran and alkyl alcohols containing 1-3 carbon atoms (washing step (b1-2)). The solvent used for washing is preferably a mixed liquid of water with acetonitrile As a mixing proportion thereof, mention may be made of, for example, the content of acetonitrile being 35-45 vol. %, preferably 39.5-40.5 vol. % relative to the entire mixed liquid. The temperature of the reverse phase SPE cartridge is preferably in the range of 19-34° C., more preferably in the range of 20-30° C. The washing step may be repeated several times, and it is preferred in this instance that water is used to wash the reverse phase SPE cartridge. As a result, unwanted solvents or reagents for deprotection can be removed whilst the radioactive fluorine labeled flutemetamol is retained in the reverse phase SPE cartridge.

Thereafter, the radioactive fluorine labeled flutemetamol is eluted from the reverse phase SPE cartridge by use of ethanol (eluting step (b1-3)). After that, water may further be passed therethrough and combined with the eluate. Further, nitrogen gas may be allowed to flow into the reverse phase SPE cartridge from an injection port thereof, or suction may be applied to an outlet thereof.

The Third Purification Step (b2)

In the third purification step (b2), the radioactive fluorine labeled flutemetamol is purified using a hydrophilic interaction-type (HILIC) solid phase extraction cartridge after the second purification step (b1).

As the HILIC solid phase extraction cartridge, can be used, for example, one which is packed with a silica gel or a silica gel to which a highly-polar functional group such as amino, amide, cyano, diol, polysuccinimide derivatives, zwitterions and cyclodextrins is introduced, and is preferably used one with a silica gel-based amino solid support, and is more preferably used one packed with an aminopropyl-modified silica gel. As a result, impurities can be captured by the HILIC solid phase extraction cartridge whilst the radioactive fluorine labeled flutemetamol is passed therethrough. Such a HILIC solid phase extraction cartridge is commercially available from, for example, Waters and Agilent Technologies. The HILIC solid phase extraction cartridge is preferably conditioned by passing therethrough acetonitrile or ethanol, and then drying by allowing nitrogen to flow thereinto prior to use.

Then, the eluate obtained in the second purification step (b1) is passed through the HILIC solid phase extraction cartridge, as it is. After that, water may be passed therethrough and combined with the eluate. Further, nitrogen gas may be allowed to flow into the HILIC solid phase extraction cartridge from an injection port thereof, or suction may be applied to an outlet thereof.

To the obtained eluate, may be added a pharmaceutically acceptable carrier, diluent, emulsion, excipient, filler, dispersant, buffer, preservative, solubilizer, antiseptic, colorant, stabilizer or the like so as to formulate a dosage form suitable for administering the radioactive fluorine labeled flutemetamol to living body, preferably an injection.

Examples of formulation for radioactive fluorine labeled flutemetamol are disclosed in, for example, WO2009/027452. The contents of WO2009/027452 are incorporated herein by reference,

EXAMPLES

Hereinafter, the present invention is explained in more detail by way of description of Examples, but the present invention is not limited thereto. Meanwhile, the reagents and column members used in the Examples were constituents of the radiopharmaceutical synthesis platform "FASTlab™" (dedicated to flutemetamol synthesis) manufactured by GE Healthcare Limited, or equivalents thereto.

(1) Study of Temperature Conditions of Radiofluorination Reaction

[$^{18}$F]fluoride ion-containing [$^{18}$O]water obtained by proton-bombardment of [$^{18}$O]water with a cyclotron was passed through an anion exchange column to adsorb and collect [$^{18}$F]fluoride ions. After the column was rinsed with water (3 mL), [$^{18}$F]fluoride ions were eluted into a colorless glass vial (5 mL) with a 0.15 mol/L aqueous solution (0.35 mL) of tetrabutylammonium hydrogen carbonate and acetonitrile (1 mL). The thus-obtained eluate was evaporated, and supplemented with a solution (1 mL) in dimethylsulfoxide of 6-ethoxymethoxy-2-(4'-(N-formyl-N-methyl)amino-3'-nitro)phenylbenzothiazole (AH111907) (75 μmol), and the vial was heated with an air heater at a set temperature shown in Table 1 whilst the reaction solution was sampled using a capillary at each time point shown in Table 1 and was subjected to determination of a labeling ratio by TLC method. The results are shown in Table 1 and FIG. 1.

The TLC method used for the determination of the labeling ratio was as follows:

TLC Analysis Conditions:
TLC plate: Silica Gel 60 $F_{254}$ (tradename, manufactured by Merck).
Mobile phase: ethyl acetate/diethylamine=100/1
Detector: Rita Star (tradename, manufactured by Raytest)

The internal temperature of the reaction solution was measured by a thermocouple.

TABLE 1

| Set temperature | Internal temperature | \multicolumn{7}{c}{Reaction time} |
|---|---|---|---|---|---|---|---|---|
| | | 3 min | 5 min | 6 min | 7 min | 9 min | 11 min | 13 min |
| 150° C. | 130° C. | 62% | — | 68% | 72% | 74% | 75% | 78% |
| 170° C. | 146° C. | 81% | 82% | — | 83% | 81% | 81% | 85% |
| 190° C. | 162° C. | 86% | — | 84% | 84% | 83% | 78% | 79% |

From Table 1 and FIG. 1, it is evident that when radiofluorination reaction is conducted at an internal temperature of about 140° C. or higher, a high labeling ratio is attained within 10 minutes from the initiation of the reaction.

(2) Study of Water Content in the Radiofluorination Reaction

Examples 1-4

(a) Radiofluorination Step

Radiofluorination reaction was carried out in the same manner as in the above section (1), except that the addition amount of the 0.15 mol/L aqueous solution of tetrabutylammonium hydrogen carbonate was 0.32-0.35 mL, water was added to the dimethylsulfoxide solution so as to meet the water content shown in Table 2, the internal temperature was set to 151° C., and the reaction time was 5 minutes.

(a1) Precursor Decomposition Step

The reaction solution obtained in the step (a) was cooled, and then supplemented with a methanol solution (11% (w/v), 1.0-1.5 mL) of sodium methoxide and heated at an internal temperature of 125° C. for 5.5 minutes, followed by cooling.

(a2) The First Purification Step

The reaction solution obtained in the step (a1) was cooled, and then supplemented with water (2 mL). The resultant mixture was passed through a triacontyl-silylated silica gel (C30) column so as to retain $^{18}$F-labeled intermediate therein. Further, the C30 column was rinsed by passing a 40% (v/v) acetonitrile aqueous solution (6 mL) therethrough via the reaction vial, and then the C30 column was rinsed again by passing a 40% (v/v) acetonitrile aqueous solution (6 mL) therethrough directly. Then, ethanol (2 mL) was passed through the C30 column so as to collect the eluate.

(b) Deprotection Step

The eluate recovered in the step (a2) was supplemented with a 4 mol/L hydrochloric acid (2.0 mL), and heated at an internal temperature of 132° C. for 3 minutes to obtain an unpurified [$^{18}$F]flutemetamol solution.

(b1) The Second Purification Step

The unpurified [$^{18}$F]flutemetamol solution obtained in the step (b) was cooled, and then supplemented with water (10 mL). The resultant mixture was passed through a fresh C30 column which had not been used in the step (a1), so as to retain [$^{18}$F]flutemetamol in the C30 column. The C30 column was rinsed by passing a 40% (v/v) acetonitrile aqueous solution (6-12 mL) therethrough, and then rinsed by passing water (5 mL) therethrough. Then, [$^{18}$F]flutemetamol was eluted with ethanol (3.5 mL) from the C30 column.

(b2) The Third Purification Step

The eluate obtained in the step (b1) was passed through a column (NH$_2$ column) packed with an aminopropyl-silylated silica gel. Water (9.3 mL) was passed through the C30 column used in the step (b1) and the NH$_2$ column in this order for rinsing. Each eluate was collected in a container in which a 18.8 mmol/L phosphate buffer solution (37.2 mL) containing 0.7% (w/v) polysorbate 80 and 1.2% (w/v) sodium chloride had been placed.

Reference Examples 1-3

Experiments were conducted in the same manner as in the Examples, except that the water content was 10 ppm, the internal temperature was set to 130° C., and the reaction time was 15 minutes, in the radiofluorination step (a).

Comparative Examples 1 and 2

The steps (a) and (a1) as in Reference Examples 1-3 were carried out, and then the following steps were carried out.

(b') Deprotection Step

The reaction solution obtained in the step (a1) was supplemented with a 4 mol/L hydrochloric acid (0.6 mL), and heated at 125° C. for 5 minutes to obtain an unpurified [$^{18}$F]flutemetamol solution.

(a2') The First Purification Step

The unpurified [$^{18}$F]flutemetamol solution obtained in the step (b') was cooled, and then supplemented with water (2 mL). The resultant mixture was passed through a C30 column so as to retain [$^{18}$F]flutemetamol. Further, the C30 column was rinsed by passing a 40% (v/v) acetonitrile aqueous solution (12 mL) therethrough via the reaction vial, and then the C30 column was rinsed by passing water (5 mL) therethrough directly. Then, acetonitrile (2 mL) was passed through the C30 column so as to collect the eluate.

(b1') The Second Purification Step

The eluate obtained in the step (a2') was passed through a NH$_2$ column for purification, and acetonitrile (1 mL) was passed therethrough. These eluates were combined together.

(b2') The Third Purification Step

The solution obtained in the step (b1') was supplemented with water (5 mL), and was passed through a fresh C30 column which had not been used in the step (a2') so as to retain [$^{18}$F]flutemetamol in the C30 column. Then, water (4 mL) was passed through the C30 column three times for rinsing. Further, ethanol (3.5 mL) was passed through the C30 column, and then water (9.3 mL) was passed through the C30 column. These eluates were collected in a container in which a 18.8 mmol/L phosphate buffer solution (37.2 mL) containing 0.7% (w/v) polysorbate 80 and 1.2% (w/v) sodium chloride had been placed.

The results of Examples 1-4, Reference Examples 1-3 and Comparative Examples 1 and 2 are shown in Table 2. In Table 2, "radioactivity (MBq)" refers to a radioactivity at the time of initiation of synthesis of [$^{18}$F]fluoride ions used in each of Examples, Reference Examples and Comparative Examples, "synthesis time (minutes)" refers to a period of time required for completing each of Examples, Reference Examples and Comparative Examples, "yield (%)" refers to a decay-corrected radiochemical yield of [$^{18}$F]flutemetamol relative to [$^{18}$F]fluoride ions, and "total amount of non-radioactive impurities (µg/mL)" refers to a concentration of the non-radioactive impurities in the obtained [$^{18}$F]flutemetamol solution.

Meanwhile, the concentration of the non-radioactive impurities in the obtained [$^{18}$F]flutemetamol solution was analyzed in a manner described below.

Analysis of Concentration of Non-Radioactive Impurities in [$^{18}$F]flutemetamol Solution The analysis was conducted by a HPLC method using a UV detector. The conditions were as follows:

Column: LunaC18(2) (manufactured by Phenomenex, size: 4.6×150 mm, 3 µm).

Mobile phase: 20 mmoL ammonium acetate buffer solution (pH 6.0)/acetonitrile=62/38→40/10 (0→9 minutes), 40/10→10/90 (9→10 minutes), 10/90 (10→20 minutes), 10/90→62/38 (20→20.5 minutes), 62/38 (20.5→30 minutes).

Flow rate: 1.0 mL/minute

Detector: Ultraviolet visible spectrometer (detection wavelength: 330 nm)

TABLE 2

|  | Radioactivity (MBq) | Synthesis time (minutes) | Water content (ppm) | Yield (%) | Total amount of non-radioactive impurities (µg/mL) |
| --- | --- | --- | --- | --- | --- |
| Example 1 | 2130 | 43 | 10*$^1$ | 69.0% | 1.87 |
| Example 2 | 2120 | 42 | 10*$^1$ | 66.3% | 1.61 |
| Example 3 | 1930 | 42 | 1000*$^2$ | 62.8% | 1.61 |
| Example 4 | 1930 | 42 | 2000*$^3$ | 58.5% | 1.98 |
| Reference Example 1 | 1570 | 56 | 10*$^1$ | 52.9% | 2.62 |
| Reference Example 2 | 1559 | 54 | 10*$^1$ | 56.0% | 1.98 |
| Reference Example 3 | 1121 | 54 | 10*$^1$ | 55.5% | 1.66 |

TABLE 2-continued

| | Radioactivity (MBq) | Synthesis time (minutes) | Water content (ppm) | Yield (%) | Total amount of non-radioactive impurities (μg/mL) |
|---|---|---|---|---|---|
| Comparative Example 1 | 1508 | 73 | 10*[1] | 41.0% | 1.82 |
| Comparative Example 2 | 1054 | 66 | 10*[1] | 30.3% | 0.69 |

Note:
*[1] A standard value of water content of DMSO manufactured by Wako Pure Chemical Industries, Ltd.
*[2] 100 mL of DMSO manufactured by Wako Pure Chemical Industries, Ltd. supplemented with 100 μL of water.
*[3] 100 mL of DMSO manufactured by Wako Pure Chemical Industries, Ltd. supplemented with 200 μL of water.

As shown in Table 2, the yield of [$^{18}$F]flutemetamol was improved, the synthesis time was shortened, and no substantial increase of the total amount of impurities was observed, in the process of Examples 1-4. Therefore, it has been shown that, according to the present invention, productivity is enhanced compared with conventional processes whilst [$^{18}$F]flutemetamol is obtained with comparable quality.

The invention claimed is:

1. A process for producing a radioactive fluorine labeled flutemetamol, which comprises:
   (a) reacting a labeling precursor of formula (1)

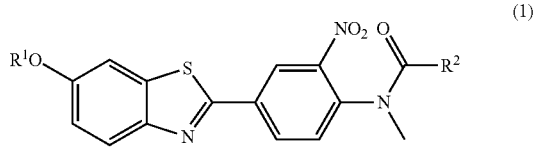
(1)

with a radioactive fluoride ion in a presence of a solvent to obtain a radioactive fluorine labeled intermediate of formula (2)

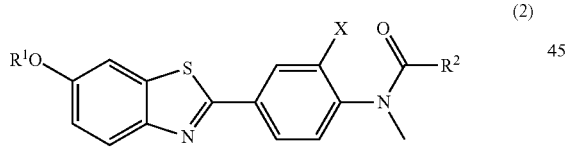
(2)

wherein R$^1$ is a hydroxy protecting group, and C(O)R$^2$ is an amino protecting group and X is a radioactive fluorine, and the solvent temperature is greater than 140° C. during the reaction; and
   (b) removing the protecting groups from the radioactive fluorine labeled intermediate to obtain a radioactive fluorine labeled flutemetamol.

2. The process according to claim 1, in which the above step (a) is carried out for a reaction time of 3-10 minutes.

3. The process according to claim 1, in which the solvent in the above step (a) comprises an organic solvent and water, and includes water in a concentration of 2000 ppm or lower.

4. The process according to claim 3, in which the solvent is dimethylsulfoxide.

5. The process according to claim 1, in which the temperature of the solvent is 145-170° C. during the reaction.

6. The process according to claim 1, wherein the process is conducted in an automated radiopharmaceutical synthesis platform configured for flutemetamol synthesis.

7. The process according to claim 3, in which the solvent is selected from acetonitrile, dimethylformamide, dimethylsulfoxide, dimethylacetamide, tetrahydrofuran, dioxane, 1,2-dimethoxyethane, sulfolane, N-methylpyrrolidone, 1-ethyl-3-methylimidazolium hexafluorophosphate, or 1-butyl-4-methylpyridinium tetrafluoroborate.

8. The process according to claim 3, in which the solvent is an imidazolium derivative, pyridinium derivative, or a tetraalkylammonium compound.

9. A process for producing a radioactive fluorine labeled flutemetamol, which comprises:
   (a) reacting a labeling precursor of formula (1)

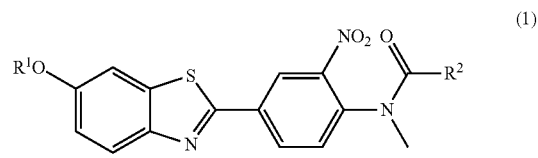
(1)

with a radioactive fluoride ion in a presence of a solvent and water to obtain a radioactive fluorine labeled intermediate of formula (2)

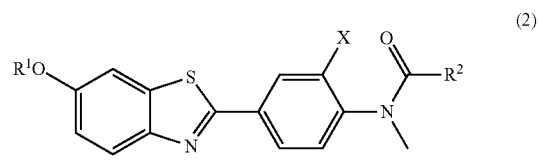
(2)

wherein R$^1$ is a hydroxy protecting group, and C(O)R$^2$ is an amino protecting group and X is a radioactive fluorine, the temperature of the solvent is 145-170° C. during the reaction; and
   (b) removing the protecting groups from the radioactive fluorine labeled intermediate to obtain a radioactive fluorine labeled flutemetamol.

10. The process according to claim 9, in which the above step (a) is carried out for a reaction time of 3-10 minutes.

11. The process according to claim 9, in which the solvent in the above step (a) includes water in a concentration of 2000 ppm or lower.

12. The process according to claim 9, in which the solvent is dimethylsulfoxide.

13. The process according to claim 9, wherein the process is conducted in an automated radiopharmaceutical synthesis platform configured for flutemetamol synthesis.

14. The process according to claim 9, in which the solvent is selected from acetonitrile, dimethylformamide, dimethylsulfoxide, dimethylacetamide, tetrahydrofuran, dioxane, 1,2-dimethoxyethane, sulfolane, N-methylpyrrolidone, 1-ethyl-3-methylimidazolium hexafluorophosphate, or 1-butyl-4-methylpyridinium tetrafluoroborate.

15. The process according to claim 9, in which the solvent is an imidazolium derivative, pyridinium derivative, or a tetraalkylammonium compound.

* * * * *